United States Patent [19]

Uyeo et al.

[11] 4,233,216
[45] Nov. 11, 1980

[54] AZETIDINONE DERIVATIVES AND PRODUCTION THEREOF

[75] Inventors: Shoichiro Uyeo; Mitsuru Yoshioka; Teruji Tsuji, all of Osaka; Ikuo Kikkawa; Wataru Nagata, both of Hyogo, all of Japan

[73] Assignee: Shionogi & Co., Ltd., Osaka, Japan

[21] Appl. No.: 967,007

[22] Filed: Dec. 6, 1978

Related U.S. Application Data

[63] Continuation-in-part of Ser. No. 875,907, Feb. 7, 1978, abandoned.

[30] Foreign Application Priority Data

Feb. 8, 1977 [JP] Japan .................................. 52/13452

[51] Int. Cl.² .................. C07D 205/08; C07D 403/12; C07D 417/12; C07D 409/12
[52] U.S. Cl. .................................... 260/239 A; 544/90
[58] Field of Search ................. 260/239 AL, 332.2 H, 260/247.3, 245.4

[56] References Cited

U.S. PATENT DOCUMENTS

| | | | |
|---|---|---|---|
| 3,988,450 | 10/1976 | James | 260/239 A |
| 4,070,477 | 1/1978 | Evret et al. | 260/306 X |
| 4,133,807 | 1/1979 | Re et al. | 260/239 A |
| 4,143,038 | 3/1979 | Narisada et al. | 260/239 A |
| 4,159,984 | 7/1979 | Yoshioka et al. | 260/239 A |

FOREIGN PATENT DOCUMENTS 1455016 11/1976 United Kingdom .

OTHER PUBLICATIONS

Wolfe et al., Tet. Letters 1973, 5131–5134.
Cama et al., J. Amer. Chem. Soc. 96, 7582–7585 (1974).
Christiansen et al., Chem. Abs. 81, 37560f (1974).

*Primary Examiner*—Mark L. Berch
*Attorney, Agent, or Firm*—Wenderoth, Lind & Ponack

[57] ABSTRACT

α-[3(R)-Substituted amino-4(R)-substituted alkoxy-2-oxo-azetidin-1-yl]-α-isopropenylacetate (Ia) and α-[3(R)-substituted amino-4(R)-substituted alkoxy-2-oxo-azetidin-1-yl]-α-isopropylideneacetate (Ib) prepared from (1R,5S)-α-(3-substituted-7-oxo-4-oxa-2,6-diazabicyclo[3.2.0]hept-2-en-6-yl)-α-isopropenylacetate or (1R,5S)-α-(3-substituted-7-oxo-4-oxa-2,6-diazabicyclo-[3.2.0]hept-2-en-6-yl)-α-isopropylideneacetate with a primary alcohol in the presence of an acid. The products are useful intermediates for preparing oxadethiacephalosporins.

12 Claims, No Drawings

AZETIDINONE DERIVATIVES AND PRODUCTION THEREOF

This invention relates to novel azetidinone derivatives useful as intermediates for synthesizing oxadethiacephalosporins. Further, it relates to a process for their preparation.

Certain azetidinone compounds have been described by Stoodley et al.: J. Chem. Soc. Perkin I, 1974, 185. Their compounds have different structures and configurations from those of this invention.

The azetidinone derivatives of this invention are represented by the formula Ia or Ib.

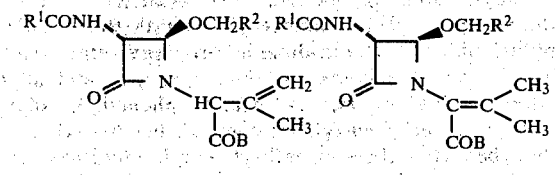

wherein
$R^1$ is alkyl, aryloxyalkyl, aralkyl, alkoxy, alkoxycarbonyl, arylcarbamoyl or aryl;
$R^2$ is —C≡CX (wherein X is hydrogen or halogen) or —C(=Y)CH$_2$Z (wherein Y is oxo or a group convertible to oxo and Z is hydrogen or a nucleophilic group), and
COB is carboxy or protected carboxy group.

The compounds of this invention are α-(2-oxo-azetidin-1-yl)-α-isopropenylacetates (Ia) and α-(2-oxo-azetidin-1-yl)-α-isopropylideneacetates (Ib), both of which have a substituted amino group ($R^1$CONH—) at position 3 in R configuration and a substituted alkoxy group ($R^2$CH$_2$O—) at position 4 in R configuration.

Typical examples of $R^1$ include $C_{1-6}$ alkyl (e.g. methyl, ethyl, propyl, isopropyl, butyl, t-butyl, cyclopentylmethyl), $C_{7-9}$ aryloxyalkyl (e.g. phenoxymethyl, phenoxyethyl, phenoxypropyl), $C_{7-15}$ aralkyl (e.g. benzyl, phenethyl, diphenylmethyl), $C_{1-6}$ alkoxy (e.g. methoxy, ethyoxy, propoxy, cyclopropylmethoxy, cyclohexyloxy), $C_{2-7}$ alkoxycarbonyl (e.g. methoxycarbonyl, ethoxycarbonyl), $C_{7-11}$ arylcarbamoyl (e.g. phenylcarbamoyl), $C_{6-10}$ aryl (e.g. phenyl, naphthyl) and the like.

The above exemplified group having alkyl residue may be substituted with halogen, carboxy, protected carboxy, nitro and the like and the group having aryl residue may be substituted with halogen, nitro, $C_{1-4}$ alkoxy, $C_{1-4}$ alkyl, hydroxy, $C_{2-5}$ acyloxy, $C_{2-5}$ acylamino, oxo and the like. The aryl residue of said groups can be five or six membered carbocyclic or heterocyclic aromatic group including phenyl, naphthyl, furyl, thienyl, pyrrolyl, oxazolyl, isoxazolyl, oxadiazolyl, oxatriazolyl, thiazolyl, isothiazolyl, thiadiazolyl, thiatriazolyl, pyrazolyl, imidazolyl, triazolyl, tetrazolyl, pyridyl, pyrimidyl, pyrazinyl, pyridazinyl, triazinyl, quinolyl, isoquinolinyl, and benzothiazolyl.

The preferred $R^1$ are $C_{1-5}$ alkyl, phenoxy-$C_{1-3}$-alkyl, phenyl-$C_{1-3}$ alkyl, $C_{1-4}$ alkoxy, $C_{1-5}$ alkoxycarbonyl, phenylcarbamoyl, phenyl, furyl, thienyl and naphthyl. In the above examples of $R^1$, phenyl may be substituted with $C_{1-5}$ alkyl, $C_{1-5}$ alkoxy, hydroxy, nitro, halogen, $C_{1-5}$ acyloxy, $C_{1-5}$ acylamino and the like.

The more preferable group are $C_{1-5}$ alkyl, phenoxy-$C_{1-3}$-alkyl, phenyl-$C_{1-3}$ alkyl, phenyl, tolyl, methoxyphenyl, chlorophenyl, nitrophenyl, hydroxyphenyl, acetoxyphenyl, acetamidophenyl, thienyl, and furyl. The most preferred $R^1$ are methyl, benzyl, phenoxymethyl and phenyl, especially benzyl and phenyl.

Furthermore, any group in the amide group at 6 and 7 position of natural or synthetic penicillins and cephalosporins is available as the group $R^1$CO of the compounds Ia and Ib, and any acyl side-chain used in synthesis of the antibiotics is also applicable to this invention. The group $R^1$ is variable widely as long as it exerts no adverse effect to the reaction, since the group is optionally removed or introduced at any stage of the synthesis to obtain the final 1-oxadethiacephalosporins. Such optional change of the group $R^1$ is included in this invention.

Specific examples of $R^1$ group include methyl, ethyl, propyl, isopropyl, butyl, methoxymethyl, carbethoxy, trichloroethoxycarbonyl, acetoxyethyl, chloroethyl, allyl, benzyl, nitrobenzyl, chlorobenzyl, aminobenzyl, acetamidobenzyl, bromobenzyl, methoxybenzyl, ethoxybenzyl, methylenedioxybenzyl, trimethoxybenzyl, dichlorobenzyl, hydroxybenzyl, phenethyl, chlorophenethyl, methylphenethyl, nitrophenethyl, methoxyphenethyl, diphenylmethyl, α-chlorobenzyl, α-bromobenzyl, α-protected carboxybenzyl, α-protected carboxybenzyl, α-protected carboxy phenethyl, acetyloxybenzyl, furylmethyl, thienylmethyl, oxazolylmethyl, isoxazolylmethyl, thiazolylmethyl, thiadiazolylmethyl, pyrazolylmethyl, tetrazolylmethyl, α-carbalkoxy-α-thienylmethyl, benzyloxycarbonyl, phenoxymethyl, phenoxyethyl, phenyoxypropyl, phenoxybutyl, isoxazolyloxymethyl, phenyl, tolyl, xylyl, hydroxyphenyl, acetoxyphenyl, methoxyphenyl, t-butyloxyphenyl, nitrophenyl, cyanophenyl, carbethoxyphenyl, aminophenyl, acetamidophenyl, methylaminophenyl, chlorophenyl, bromophenyl, thienyl, furyl, pyrrolyl, oxazolyl, oxadiazolyl, oxatriazolyl, thiazolyl, thiadiazolyl, pyrazolyl, triazolyl, tetrazolyl, pyridyl, t-butoxy, cyclopropylmethoxy, cyclopropylethoxy, cyclopentyloxy, methanesulfonylethoxy, and trichloroethoxy.

The group $R^2$ is alkynyl represented by the formula —C≡CX wherein X is hydrogen or halogen (e.g. bromine and chlorine) and —C(=Y)CH$_2$Z wherein Y is oxo or a group convertible to oxo by ozonization (e.g. methylene and substituted methylene such as diphenylmethylene and methoxycarbonylmethylene) and Z is hydrogen or a nucleophilic group (e.g. halogen, $C_{1-6}$ alkoxy, $C_{1-5}$ acyloxy, non-carbon acyloxy, $C_{1-5}$ alkylthio, $C_{6-10}$ arylthio and hydroperoxy). Non-carbon acyloxy means a acyloxy group not having carbon atom such as nitrooxy, sulfurousoxy, sulfenyloxy, sulfinyloxy and the like.

The typical examples of the nucleophilic group are halogen, (e.g. bromine, chlorine), $C_{1-6}$ alkoxy (e.g. methoxy, ethoxy, butoxy, cyclohexyloxy, cyclopropylmethoxy, tetrahydropyranyloxy), $C_{1-7}$ acyloxy (e.g. formyloxy, acetoxy, propionyloxy, trifluoroacetoxy, β-hydroxypropionyloxy, α-haloacetyloxy, β-hydroxypropionyloxy, benzoyloxy, nicotinoyloxy, carbamoyloxy, methoxycarbonyloxy, aminopropionyloxy), non-carbon acyloxy (e.g. nitrooxy, sulfurousoxy, sulfenyloxy, sulfinyloxy), $C_{1-5}$ alkylthio (e.g. methylthio, ethylthio, butylthio, cyclopropylthio), $C_{6-10}$ arylthio (e.g. phenylthio, naphthylthio, thienylthio, 1-methyltetrazolylthio, 1-methanesulfonylethyl-5-tetrazolylthio, 1-carboxyethyl-5-tetrazolylthio, 1-protected carboxyethyl-5-tetrazolylthio, 1-protected sulfonylethyl-5-tetrazolylthio, 1-methylaminoethyl-5-tetrazolylthio, 1-dimethylaminoethyl-5-tetrazolylthio, 1-dimethylaminoethyl-5-tetrazolylthio, 1-morpholinoethyl-5-tetrazolylthio, 1,3,4-thiadiazol-5-ylthio, 2-methyl-1,3,4-thiadiazol-5-yl-thio, 2-carboxymethyl-1,3,4-thiadiazol-5-ylthio, 2-protected carboxymethyl-1,3,4-thiadiazol-5-ylthio, 2-protected hydroxymethyl-1,3,4-thiadiazol-5-ylthio, 2-aminomethyl-1,3,4-thiadiazol-5-ylthio, 2-methylaminomethyl-1,3,4-thiadiazol-5-ylthio, 1,2,3-triazol-4-ylthio, 1-methyl-5-hydroxy-6-oxo-1,6-dihydro-1,3,4-triazin-2-ylthio) and hydroperoxy.

The preferred $R^2$ are ethynyl, halogenoethynyl, acetyl, halogenoacetyl, $C_{1-4}$ alkoxy-acetyl, $C_{1-5}$ acyloxyacetyl, $C_{1-4}$ alkylthio-acetyl, phenylthioacetyl, (5-membered heterocyclic thio)acetyl, hydroperoxyacetyl, isopropenyl, 1-methylene-2-halogenoethyl, 1-methylene-2-$C_{1-4}$ alkoxy-ethyl, 1-methylene-2-$C_{1-5}$ acyloxy-ethyl, 1-methylene-2-$C_{1-4}$ alkylthio-ethyl, 1-methylene-2-phenylthioethyl, 1-methylene-2-(5-membered heterocyclic thio)ethyl, 1-methylene-2-hydroperoxyethyl, 1-diphenylmethylene-ethyl, 1-diphenylmethylene-2-halogenoethyl, 1-diphenylmethylene-2-$C_{1-4}$ alkoxyethyl, 1-diphenylmethylene-2-$C_{1-5}$ acyloxyethyl, 1-diphenylmethylene-2-$C_{1-4}$ alkylthio-ethyl, 1-diphenylmethylene-2-phenylthioethyl, 1-diphenylmethylene-2-(5-membered heterocyclic thio)-ethyl, 1-diphenylmethylene-2-hydroxyperoxyethyl, 1-methoxycarboxylmethylene-ethyl, 1-methoxycarbonylmethylene-2-halogeno-ethyl, 1-methoxycarbonylmethylene-2-$C_{1-4}$ alkoxy-ethyl, 1-methoxycarbonylmethylene-2-$C_{1-5}$ acyloxy-ethyl, 1-methoxycarbonylmethylene-2-$C_{1-4}$ alkylthio-ethyl, 1-methoxycarbonylmethylene-2-phenylthioethyl, 1-methoxycarbonylmethylene-2-(5-membered heterocyclic thio)-ethyl and 1-methoxycarbonylmethylene-2-hydroperoxyethyl. Preferable 5-membered heterocyclic groups are tetrazolyl and thiadiazolyl.

The more preferable illustrative of the group $R^2$ are ethynyl, 2-bromoethynyl, acetoxyacetyl, (1-methyltetrazol-5-yl)thioacetyl, (2-methyl-1,3,4-thiadiazol-5-yl)thioacetyl, 1-methylene-2-acetoxyethyl, 1-methylene-2-(1-methyltetrazol-5-yl)thioethyl, 1-methylene-2-(2-methyl-1,3,4-thiadiazol-5-yl)thioethyl, 1-methoxycarbonylmethylene-2-(1-methyltetrazol-5-yl)thioethyl and the like.

The most preferred $R^2$ are ethynyl, 2-bromoethynyl, (1-methyltetrazol-5-yl)thioacetyl, 1-methylene-2-acetoxyethyl, 1-methoxycarbonylmethylene-2-(1-methyltetrazol-5-yl)thioethyl, especially ethynyl. Acetoxyacetyl is also a most preferred $R^2$.

This invention includes free carboxy acids and the corresponding carboxy-protected compounds. The carboxy protecting group (shown by B in the above formula Ia and Ib) is those generally used in synthetic chemistry in β-lactam compounds, for example, ester residue such as $C_{1-5}$ alkoxy (e.g. methoxy ethoxy, t-butoxy), $C_{7-20}$ aralkyloxy (e.g. benzyloxy, diphenylmethoxy, trityloxy), $C_{6-10}$ aryloxy (e.g. phenyloxy, indanyloxy, naphthyloxy), $C_{3-10}$ organometallic oxy (e.g. trimethylsilyloxy, ethoxydimethylsilyloxy, trimethylstannyloxy), $C_{1-15}$ alkylamino (e.g. dimethylamino, dibutylamino, diisopropylhidrazino), ammonium oxy (e.g. triethylammonium oxy), alkali metal oxy (e.g. sodium oxy, potassium oxy, lithium oxy), alkaline earth metal oxy (e.g. magnesium oxy, calcium oxy), aluminium oxy and the like.

The above protecting group may have substituents such as halogen, hydroxy, $C_{1-5}$ acyloxy, $C_{1-4}$ alkoxy, oxo, $C_{1-5}$ acylamino, nitro, $C_{1-4}$ alkyl and the like. Aromatic heterocyclic residues are included in the term aryl. The carboxy protecting group is widely variable as long as it serves for the protection.

Specific examples of COB group include those forming optionally substituted alkyl esters, e.g. methyl, ethyl, isopropyl, propyl, butyl, pentyl, cyclopropylmethyl, cyclopropylethyl, cyclopropylbutyl, monohydroxy-t-butyl, trichloroethyl, chloromethyl, cyanomethyl, methanesulfonylethyl, acetylmethyl, diacetylmethyl, acetoxymethyl, propionyloxymethyl, benzoyloxymethyl, methoxymethyl, methoxyethoxymethyl, carbethoxymethyl, phenoxymethyl, methylthiomethyl, phenylthiomethyl, tetrahydropyranyl, phthalimidomethyl, α,α-dimethylpropargyl, ethoxycarbonyloxyethyl, methoxycarbonyloxypropyl, and allyl esters; aralkyl esters, e.g. benzyl, phenethyl, tolylmethyl, dimethylbenzyl, nitrobenzyl, halobenzyl, methoxybenzyl, phthalidyl, anthrylmethyl, p-hydroxy-3,5-di-t-butylbenzyl, diphenylmethyl, methoxydiphenylmethyl, trityl, phenacyl, chlorophenacyl, bromophenacyl, nitrophenacyl, and methylphenacyl esters; aromatic esters, e.g. phenyl, naphthyl, tolyl, dimethylphenyl, nitrophenyl, methanesulfonylphenyl, chlorophenyl, pentachlorophenyl, indanyl, and pyridyl esters; organometallic esters, e.g. trimethylsilyl, dimethylmethoxysilyl, methylenedioxymethylsilyl, trimethylstannyl esters; alkali metal or alkaline earth metal salts, e.g. sodium, potassium, lithium, magnesium, calcium, barium, acyloxycalcium, and organic base salts, e.g triethylammonium and bicyclohexylammonium salt.

The preferable definition of the group B are hydroxy, $C_{1-4}$ alkoxy, phenyl-$C_{1-3}$ alkoxy, diphenyl-$C_{1-3}$-alkoxy, phenoxy, indanyloxy, naphthoxy, tri-$C_{1-3}$ alkylsilyloxy, $C_{1-3}$ alkoxy di-$C_{1-3}$ alkylsilyloxy, tri-$C_{1-3}$-alkylstannyloxy, di-$C_{1-3}$ alkylhydrazino, alkali metal oxy, magnesium oxy, calcium oxy, aluminium oxy, tri-$C_{1-3}$-alkylammonium oxy, bicyclohexylammonium oxy and the like.

The more preferred definition are hydroxy, phenyl-$C_{1-3}$ alkoxy, diphenyl-$C_{1-3}$ alkoxy and $C_{1-4}$ alkoxy. The most preferred B are hydroxy, diphenylmethoxy, benzyloxy, t-butoxy, especially diphenylmethoxy.

Typical examples of Compound Ia and Compound Ib include those where (1) $R^1$ is methyl, $R^2$ is acetoxyacetyl, and B is diphenylmethoxy,
(2) $R^1$ is methyl, $R^2$ is ethynyl, and B is diphenylmethoxy,
(3) $R^1$ is methyl, $R^2$ is chloroethynyl, and B is benzyloxy,
(4) $R^1$ is methyl, $R^2$ is 1-methylene-2-acetoxyethyl, and B is methoxy,
(5) $R^1$ is methyl, $R^2$ is methylthioacetyl, and B is hydroxy,
(6) $R^1$ is methyl, $R^2$ is 1-methoxycarbonylmethylene-2-(1-methyltetrazol-5-yl)thioethyl, and B is diphenylmethoxy,
(7) $R^1$ is methyl, $R^2$ is 1-methylene-2-(2-methyl-1,3,4-thiadiazol-5-yl)thioethyl, and B is benzyloxy,
(8) $R^1$ is ethyl, $R^2$ is ethynyl, and B is diphenylmethoxy,
(9) $R^1$ is ethyl, $R^2$ is acetoxyacetyl, and B is hydroxy,
(10) $R^1$ is ethyl, $R^2$ is 1-acetoxymethylene-2-(1-methyltetrazol-5-yl)thioethyl, and B is t-butoxy,
(11) $R^1$ is isopropyl, $R^2$ is acetoxyacetyl, and B is hydroxy,

(12) $R^1$ is isopropyl, $R^2$ is 1-methylene-2-(2-methyl-1,3,4-thiadiazol-5-yl)thioethyl, and B is ethoxy,
(13) $R^1$ is isopropyl, $R^2$ is 1-diphenylmethylene-2-acetoxyethyl, and B is diphenylmethoxy,
(14) $R^1$ is t-butyl, $R^2$ is bromoethynyl, and B is benzyloxy,
(15) $R^1$ is t-butyl, $R^2$ is (1-methyltetrazolyl-5-yl)thioacetyl, and B is diphenylmethoxy,
(16) $R^1$ is t-butyl, $R^2$ is 1-methoxycarbonylmethylene-2-acetoxyethyl, and B is hydroxy,
(17) $R^1$ is phenoxymethyl, $R^2$ is ethynyl, and B is t-butoxy,
(18) $R^1$ is phenoxymethyl, $R^2$ is acetoxyacetyl, and B is diphenylmethoxy,
(19) $R^1$ is phenoxymethyl, $R^2$ is 1-methoxycarbonylmethylene-2-acetoxyethyl, and B is diphenylmethoxy,
(20) $R^1$ is phenoxymethyl, $R^2$ is 1-methylene-2-(1-methyltetrazol-5-yl)thioethyl, and B is t-butoxy,
(21) $R^1$ is methoxy, $R^2$ is ethynyl, and B is diphenylmethoxy,
(22) $R^1$ is methoxy, $R^2$ is 1-methylene-2-methoxyethyl, and B is benzyloxy,
(23) $R^1$ is methoxy, $R^2$ is 1-diphenylmethylene-2-phenylthioethyl, and B is hydroxy,
(24) $R^1$ is ethoxycarbonyl, $R^2$ is acetoxyacetyl, and B is hydroxy,
(25) $R^1$ is ethoxycarbonyl, $R^2$ is bromoethynyl, and B is diphenylmethoxy,
(26) $R^1$ is ethoxycarbonyl, $R^2$ is 1-methylnene-2-chloroethyl, and B is methoxy,
(27) $R^1$ is ethoxycarbonyl, $R^2$ is 1-methylene-2-(1-methyltetrazol-5-yl)thioethyl, and B is benzyloxy,
(28) $R^1$ is phenoxycarbamoyl, $R^2$ is ethynyl, and B is diphenylmethoxy,
(29) $R^1$ is phenoxycarbamoyl, $R^2$ is hydroperoxyacetyl, and B is hydroxy,
(30) $R^1$ is phenoxycarbamoyl, $R^2$ is 1-methylene-2-(2-methyl-1,3,4-thiadiazol-5-yl)thioethyl, and B is t-butoxy,
(31) $R^1$ is phenoxycarbamoyl, $R^2$ is 1-methoxycarbonylmethylene-2-acetoxyethyl, and B is benzyloxy,
(32) $R^1$ is benzyl, $R^2$ is ethynyl, and B is diphenylmethoxy,
(33) $R^1$ is benzyl, $R^2$ is hydroperoxyacetyl, and B is diphenylmethoxy,
(34) $R^1$ is benzyl, $R^2$ is bromoethyl, and B is diphenylmethoxy,
(35) $R^1$ is benzyl, $R^2$ is 1-methylene-2-acetoxyethyl, and B is diphenylmethoxy,
(36) $R^1$ is benzyl, $R^2$ is acetoxyacetyl, and B is diphenylmethoxy,
(37) $R^1$ is benzyl, $R^2$ is 1-methoxycarbonylmethylene-2-(1-methyltetrazolyl-5-yl)thioethyl, and B is diphenylmethoxy,
(38) $R^1$ is benzyl, $R^2$ is (1-methyltetrazol-5-yl)thioacetyl, and B is diphenylmethoxy,
(39) $R^1$ is benzyl, $R^2$ is 1-methylene-2-ethoxyethyl, and B is hydroxy,
(40) $R^1$ is benzyl, $R^2$ is ethynyl and B is hydroxy,
(41) $R^1$ is benzyl, $R^2$ is 1-methylene-2-(2-methyl-1,3,4-thiadiazol-5-yl)thioethyl, and B is t-butoxy,
(42) $R^1$ is benzyl, $R^2$ is methylthioacetyl, and B is benzyloxy,
(43) $R^1$ is benzyl, $R^2$ is 1-methoxycarbonylmethylene-2-bromoethyl, and B is hydroxy,
(44) $R^1$ is phenyl, $R^2$ is bromoethynyl, and B is diphenylmethoxy,
(45) $R^1$ is phenyl, $R^2$ is methylthioacetyl, and B is diphenylmethoxy,
(46) $R^1$ is phenyl, $R^2$ is 1-methoxycarbonylmethylene-2-(1-methyltetrazolyl-5-yl)thioethyl, and B is diphenylmethoxy,
(47) $R^1$ is phenyl, $R^2$ is acetoxyacetyl, and B is benzyloxy,
(48) $R^1$ is phenyl, $R^2$ is ethynyl, and B is hydroxy,
(49) $R^1$ is phenyl, $R^2$ is 1-methylene-2-acetoxyethyl, and B is benzyloxy,
(50) $R^1$ is phenyl, $R^2$ is (1-methyltetrazol-5-yl)thioacetyl, and B is t-butoxy,
(51) $R^1$ is phenyl, $R^2$ is 1-methoxycarbonylmethylene-2-chloroethyl, and B is hydroxy,
(52) $R^1$ is phenyl, $R^2$ is 1-diphenylmethylene-2-methylthioethyl, and B is ethoxy,
(53) $R^1$ is phenyl, $R^2$ is 1-methylene-2-ethoxyethyl, and B is methoxy,
(54) $R^1$ is methoxyphenyl, $R^2$ is acetoxyacetyl, and B is diphenylmethoxy,
(55) $R^1$ is methoxyphenyl, $R^2$ is ethynyl, and B is hydroxy,
(56) $R^1$ is methoxyphenyl, $R^2$ is 1-methylene-2-acetoxyethyl, and B is benzyloxy,
(57) $R^1$ is methoxyphenyl, $R^2$ is (1-methyltetrazol-5-yl)thioacetyl, and B is t-butoxy,
(58) $R^1$ is methoxyphenyl, $R^2$ is 1-methoxycarbonylmethylene-2-phenylthioethyl, and B is diphenylmethoxy,
(59) $R^1$ is chlorophenyl, $R^2$ is chloroethynyl, and B is benzyloxy,
(60) $R^1$ is chlorophenyl, $R^2$ is acetoxyacetyl, and B is diphenylmethoxy,
(61) $R^1$ is chlorophenyl, $R^2$ is 1-methylene-2-(1-methyltetrazol-5-yl)thioethyl, and B is t-butoxy,
(62) $R^1$ is chlorophenyl, $R^2$ is 1-diphenylmethylene-2-methoxyethyl, and B is methoxy,
(63) $R^1$ is nitrophenyl, $R^2$ is methylthioacetyl, and B is hydroxy,
(64) $R^1$ is nitrophenyl, $R^2$ is 1-methylene-2-acetoxyethyl, and B is benzyloxy,
(65) $R^1$ is hydroxyphenyl, $R^2$ is ethynyl, and B is diphenylmethoxy,
(66) $R^1$ is hydroxyphenyl, $R^2$ is 1-methoxycarbonylmethylene-2-(1-methyltetrazol-5-yl)thioethyl, and B is methoxy,
(67) $R^1$ is tolyl, $R^2$ is bromoethynyl, and B is t-butoxy,
(68) $R^1$ is tolyl, $R^2$ is acetoxyacetyl and B is hydroxy,
(69) $R^1$ is acetoxyphenyl, $R^2$ is ethynyl and B is benzyloxy,
(70) $R^1$ is acetoxyphenyl, $R^2$ is 1-methoxycarbonylmethylene-2-(2-methyl-1,3,4-thiaziazol-5-yl)thioethyl, and B is benzyloxy,
(71) $R^1$ is acetamidophenyl, $R^2$ is ethynyl, and B is hydroxy,
(72) $R^1$ is acetamidophenyl, $R^2$ is 1-methylene-2-methylthioethyl, and B is t-butoxy,
(73) $R^1$ is thienyl, $R^2$ is ethynyl, and B is diphenylmethoxy,
(74) $R^1$ is thienyl, $R^2$ is acetoxyacetyl, and B is hydroxy,
(75) $R^1$ is thienyl, $R^2$ is (1-methyltetrazol-5-yl)thioacetyl, and B is methoxy,
(76) $R^1$ is furyl, $R^2$ is ethynyl, and B is diphenylmethoxy, and
(77) $R^1$ is furyl, $R^2$ is 1-methoxycarbonylmethylene-2-(1-methyltetrazol-5-yl)thioethyl, and B is hydroxy.

The compounds Ia and Ib can be prepared by treating a compound represented by the formula IIa or IIb with an alcohol represented by the formula III.

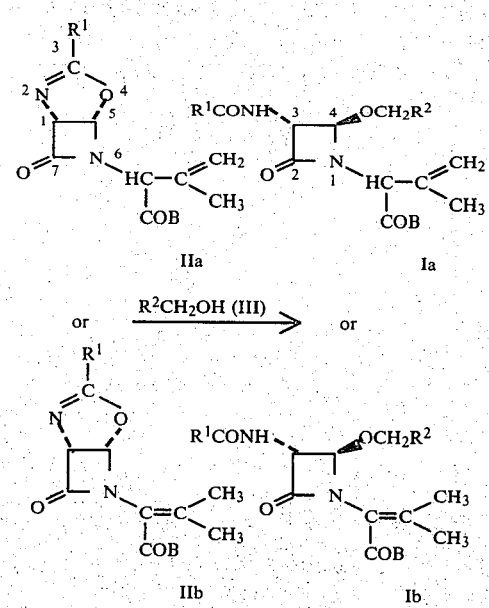

(wherein $R^1$, $R^2$ and COB each has the same meaning as defined above)

Namely, the objective compounds Ia and Ib can be prepared by the reaction of (1R,5S)-α-(3-substituted-7-oxo-4-2,6-diazabicyclo[3.2.0]hept-2-en-6-yl)-α-isopropenylacetate (IIa) or (1R,5S)-α-(3-substituted-7-oxo-4-oxa-2,6-diazabicyclo[3.2.0]hept-2-en-6-yl)-α-isopropylideneacetate (IIb) with a primary alcohol (III) in the presence of an acid. As noted above, prior art in connection with this invention is described by Stoodley et al., J. Chem. Soc. Perkin I, 1974, 185. In the said prior art, oxazoline nitrogen and oxazoline oxygen are both at β-side of the azetidine ring, i.e. reverse side from the starting compounds IIa and IIb, and methanol is used in place of the substituted alcohols (III) of this invention. The process of this invention selectively forms 4α-hydrogen on the compounds Ia and Ib instead of 4β-hydrogen as in the prior art. The 4α-hydrogen achieved therefrom results in 6α-hydrogen of 1-oxadethiacephalosporins which is a requisite of effective 1-oxadethiacephalosporins. Further, the structure of the compound Ib is suitable for cyclization to 1-oxadethiacephalosporins.

The acid used in the above reaction can be, for example, hydrochloric acid, sulfonic acid, phosphoric acid, p-toluenesulfonic acid, methanesulfonic acid, trifluoromethanesulfonic acid, boron trifluoride, aluminium chloride, titanium tetrachloride, fluorosulfonic acid, or the like. Trifluoromethanesulfonic acid and boron trifluoride are preferred.

The reaction can be effected at about $-10°$ C. to $50°$ C., and preferably around room temperature, with or without solvent such as hydrocarbons (e.g. benzene, toluene and hexane), halogenohydrocarbons (e.g. methylene chloride, dichloroethane, trichloroethane and chlorobenzene), ethers (e.g. dioxane and tetrahydrofuran), esters (e.g. ethyl acetate and amyl acetate) and the like.

After completion of the reaction, the resultant compound can be isolated and purified by a usual method such as extraction, water washing, drying, concentration, chromatography or the like.

The starting compound of this invention IIa is prepared simply by heating a 6-epi-penicillin 1-oxide represented by the following formula IV at a temperature of $70°$ C. to $130°$ C. preferably in the presence of a desulfuration agent (e.g. triarylphosphine, trialkylphosphine and trialkylphosphite).

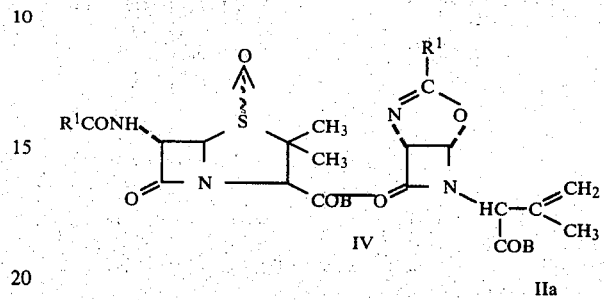

(wherein $R^1$ and COB each has the same meaning as defined above)

The compound IV can be prepared by the procedure described in J. Chem. Soc. Perkin I, 1973, 932. Another starting compound IIb is easily prepared by reacting the double bond isomer IIa with an organic base (e.g. alkylamine and aralkylamine) or an inorganic base (e.g. alkali metal hydroxide) at a temperature of $0°$ C. to $70°$ C. in an inert solvent.

Besides, the compound Ia obtained by this invention is also convertible to the compound Ib in the same manner. Thus, the compound Ia is treated with an organic base (e.g. alkylamine and aralkylamine) or an inorganic base (e.g. hydroxide and carbonate of alkali metal) in an inert solvent. The preferred bases are N-methylmorpholine, N-methylpiperidine, triethylamine, N,N-dimethylbenzylamine and the like. The said solvent is an alcohol or other organic solvent available for the reaction of the compound IIa or IIb with the compound III. The reaction is completed at a temperature of $0°$ C. to $70°$ C. for 1 minute to 5 hours.

The compound Ib is useful to prepare 1-oxadethiacephalosporins. Namely, the compound Ib is hydrated (or ozonized) and oxidized to cleave the side chain at position 1 of the azetidinone ring, then reduced, halogenated at the hydroxy of the substituent at position 1, and reacted with triphenylphosphine to give a Wittig compound. The thus obtained Wittig compound is cyclized to give a 1-oxadethiacepharosporin. A methoxy group is introduced to position 7 of the product followed by hydrolysis. The following schema exemplifies the above procedure:

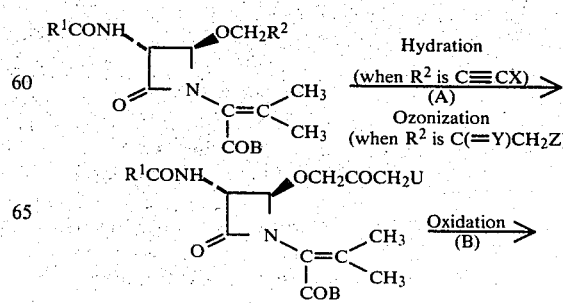

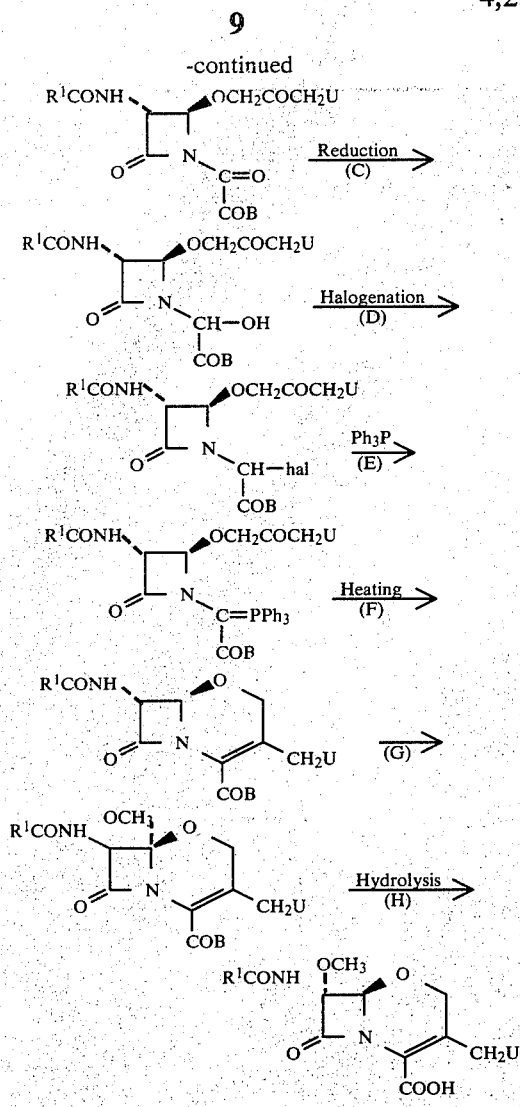

(wherein Ph is phenyl, hal is halogen, and U is X or Z and $R^1$, $R^2$, COB, X and Z each has the same meaning as defined above).

The above procedure gives 1-oxadethiacephalosporins in high yield with less side-reactions. The 1-oxadethiacephalosporins are useful antibiotics as described in Journal of Americal Chemical Society, 96, 7582 (1974).

This invention thus provides useful intermediates and a process for the synthesis of oxadethiacephalosporins.

The invention will now be further illustrated and described by way of the following examples.

EXAMPLE 1

Diphenylmethyl
α-[4(R)-propargyloxy-3(R)-phenylacetamido-2-oxo-azetidin-1-yl]-α-isopropylideneacetate To a solution of diphenylmethyl α-[(1R,5S)-benzyl-7-oxo-4-oxa-2,6-diazabicyclo[3.2.0]hept-2-en-6-yl]-α-isopropylideneacetate (54 g) in dry propargyl alcohol (50 ml) is added boron trifluoride etherate (2 ml). While following the reaction by means of thin layer chromatography, an additional amount of boron trifluoride etherate is added to the mixture (total amount 3.2–3.5 ml). After disappearance of the starting compound, the mixture is poured into a mixture of ethyl acetate (400 ml), water (400 ml) and ice pieces, stirred, and neutralized with an aqueous solution of sodium hydrogen carbonate (1–2 g). The organic layer is separated, and the aqueous layer is washed with ethyl acetate (200 ml). The organic layer combined with the washing is dried over sodium sulfate and evaporated to dryness to yield the product (50.5 g). This is chromatographed over a column of silica gel deactivated with 10% water (500 g) and eluted with a mixture of benzene and ethyl acetate (19:1 to 4:1). The residue from the eluates is mixed with ether (50 ml) to yield crystals as precipitate. The crystals are collected by filtration and recrystallized from ethyl acetate to give the title compound (20 g), mp 123.2°–124.0° C. $[\alpha]_D^{26.0} -55.7 \pm 1.0$ (chloroform; c=1.007)

NMR: $\delta_{ppm}^{CDCl_3}$ 2.00s3H, 2.23s3H, 2.18t(2.2 Hz)1H, 3.50s1H, 4.17d(2.2 )2H, 4.65dd(6.5, 1.1 Hz)1H, 5.15d(1.1Hz)1H, 6.15d(6.5 Hz)1H, 6.90s1H, 7.08–7.46 ml5H.

IR: $\nu_{max}^{CHCl_3}$ 3410, 3300, 1775, 1720, 1680 cm$^{-1}$.

EXAMPLE 2

(1) Diphenylmethyl
α-[4(R)-(3-bromopropargyloxy)-3(R)-benzoylamino-2-oxo-azetidin-1-yl]-α-isopropenylacetate Diphenylmethyl α-[(1R,5S)-3-phenyl-7-oxo-4-oxa-2,6-diazabicyclo[3.2.0]hept-2-en-6-yl]-α-isopropenylacetate (136 mg) is dissolved in 3-bromopropargyl alcohol (61 μl) under heating. To the solution is added boron trifluoride etherate (2 μl). The mixture is stirred for 45 minutes at room temperature and then kept at 0° C. for two days. The same procedure as in Example 1 is effected to give the title compound (180 mg).

NMR: $\delta_{ppm}^{CDCl_3}$ 1.83s3H, 4.20s1H, 4.33s2H, 4.80d(7 Hz)1H, 4.95–5.10m4H, 5.48s1H, 6.94s1H, 7.08–7.58 ml 5H.

IR: $\nu_{max}^{CHCl_3}$ 3420, 2210, 1775, 1735, 1657, 1595, 1580 cm$^{-1}$.

(2) Diphenylmethyl
α-[4(R)-(3-bromopropargyloxy)-3(R)-benzoylamino-2-oxo-azetidin-1-yl]-α-isopropylideneacetate The above product (180 mg) of (1) is dissolved in methylene chloride (0.5 ml) and triethylamine (41 μl) is added thereto. The mixture is stirred at room temperature for 1 hour. The solvent is removed by evaporation to give a pinnate residue. Recrystallization from a mixture of pentene and ether gives powder of the title compound (160 mg). Yield 90.8%.

NMR: $\delta^{CDCl_3}$ 2.05s3H, 2.28s3H, 4.28s2H, 4.87d(7 Hz)1H, 5.27s1H, 6.95s1H, 7.03–7.60 ml 5H.

IR: $\nu_{max}^{CHCl_3}$ 3420, 2225, 1775, 1728, 1667, 1632, 1602, 1582 cm$^{-1}$.

EXAMPLES 3–15

Compound IIa or IIb is reacted with Compound III under the conditions shown in Table 1 to give the corresponding Compound Ia or Ib. The physical constants are shown in Table 2. Meanwhile, Example II presents the physical constants of Compound Ib produced from Compound Ia by the same procedure as in Example 2(2).

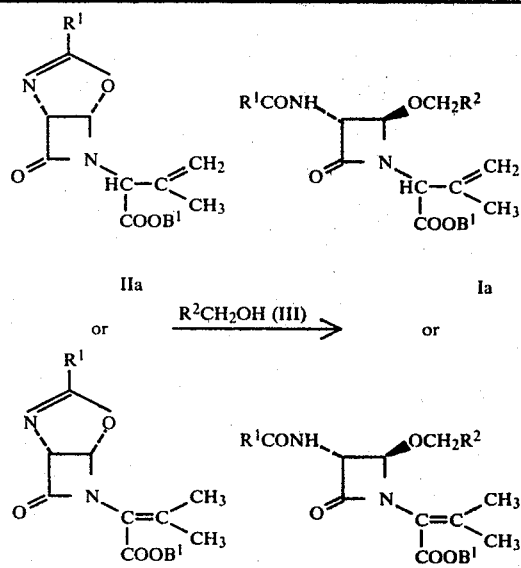

IIa or IIb → R²CH₂OH (III) → Ia or Ib

|  |  | Compound II |  |  | Compound III |  | Reaction Conditions |  |  | Product Ia or Ib Yield |  |
|---|---|---|---|---|---|---|---|---|---|---|---|
| Ex. No. | St. | R¹ | B¹ | Amount (g) | R² | Amount (ml) | Solvent (ml) | Catalytic Acid (ml) | Temp. (°C.) | Time (hr.) | (g) | (%) |
| 3 | IIb | CH₂Ph | CHPh₂ | 9.76 | CH=CH₂ | 2.7 | DM 50 | TMS 0.44 | 5-25 | 2 | 2.775 | |
| 4 | " | " | " | 59.1 | " | 180 | — | TMS 1.12 | 20-28 | 1.4 | 53.4 | 80.3 |
| 5 | " | " | " | 1.04 | C≡CBr | 0.61 | — | BTF 0.02 | r.t. | 4 | 0.804 | 44.5 |
| 6 | " | " | " | 2.89 | C(=CH₂)CH₂OAc | 2.29 | DM 25 | TMS 0.2 | " | 1 | 2 | 20 |
| 7 | " | " | " | 7.56 | COCH₂OAc | 3.75 | DM 45 | BTF 0.56 | " | overnight | 2 | 16 |
| 8 | " | " | " | 4.67 | C(=CHCOOCH₃)CH₂S-Tet | 2.44 | DM 30 | TMS 0.177 | " | 5 | 1.55 | |
| 9 | " | " | " | 0.234 | COCH₂S-Tet | 0.176 | DM 2 | BTF 0.006 | Ref. | 1.5 | 0.035 | |
| 10 | " | Ph | " | 0.100 | CH=CH₂ | 0.120 | — | BTF 0.0014 | r.t. | 5 | 0.095 | 84 |
| 11 | IIa | " | " | 0.136 | C(=CHCOOCH₃)CH₂S-Tet | 0.073 | DM 1.4 | BTF 0.019 | " | 0.75 | 0.023 | |
| 12 | " | " | " | 5.45 | CH=CH₂ | 17.11 | — | TMS 0.053 | " | 0.5 | 5.53 | 90 |
| 13 | IIb | " | CH₂Ph | 17.65 | " | 65 | — | TMS 0.206 | 20 | 0.8 | 18.60 | 75.3 |
| 14 | IIa | CH₃ | " | 0.05 | " | 0.1 | DM 1 | BTF 0.01 | r.t. | 3 | 0.01 | |
| 15 | " | CH₂OPh | C(CH₃)₃ | 0.230 | C≡CH | 0.230 | DM 1.15 | BTF 0.01 | " | 1 | 0.254 | 29 |

Notes:
The abbreviations in the above table have the following meanings.
Ph = phenyl, Ac = acetyl, Tet = 1-methyltetrazol-5-yl, DM = methylene chloride, TMS = trifluoromethanesulfonic acid, BTF = Boron trifluoride etherate, r.t. = room temperature, Ref. = Reflux, St. = Structure

TABLE 2

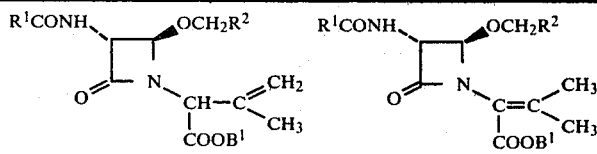

(Ia) (Ib)

| Ex. No. | St. | Compound I R¹ | B¹ | R² | IR: $\nu_{max}^{CHCl_3}$ cm⁻¹ | NMR: $\delta_{ppm}^{CDCl_3}$ (J=Hz) |
|---|---|---|---|---|---|---|
| 3,4 | Ib | CH₂Ph | CHPh₂ | —CH=CH₂ | 1776,1725,1686,1635* | 2.03s3H,2.27s3H,3,53s2H,4.00brd(6)2H, 4.75d(7.5)1H,5.00s1H,6.17d(7.5)1H, 6.97s1H,7.30s5H,7.35m10H. |
| 5 | " | " | " | —C≡CBr | 3420,2212,1778,1722, 1684,1632,1583. | 2.03s3H,2.28s3H,3.52s2H,4.21s2H,4.67 d(6)1H,5.15s1H,6.20d(6)1H,6.95s1H, 7.12-7.52m15H. |
| 6 | " | " | " | —C(=CH₂)CH₂OAc | — | 2.02brs6H,2.25s3H,3.25s2H,4.03brs2H, 4.48brs2H,4.71brd(6.5)1H,5.03m4H, 6.42brd(6.5)1H,7.00s1H,7.39aromatic15H |
| 7 | " | " | " | —COCH₂OAc | 3420,1780,1745,1730 1680. | 2.03s3H,2.13s3H,2.28s3H,3,53s2H,4.25 s2H,4.65d(6)1H,4.70s2H,5.03s1H,6.42d (6)1H,7.03s1H,7.4aromatic15H. |
|  |  |  |  |  |  | 2.05s3H,2.25s3H,3.54s2H, |

TABLE 2-continued

Structures:

(Ia): R¹CONH and OCH₂R² on azetidinone ring, N-CH-C(=CH₂)(CH₃), with COOB¹ on CH (Ib): R¹CONH and OCH₂R² on azetidinone ring, N-C=C(CH₃)(CH₃), with COOB¹

| Ex. No. | St. | R¹ | B¹ | R² | IR: $\nu_{max}^{CHCl_3}$ cm$^{-1}$ | NMR: $\delta_{ppm}^{CDCl_3}$ (J=Hz) |
|---|---|---|---|---|---|---|
| 8 | " | " | " | —C(=CHCOOCH₃)CH₂S-Tet | 3500-3300,3100-2900 1775,1710,1680,1510, 1460-1360,1360-1350 | 3.92s3H,4.27s4H,4.73brd(6.5) 1H,5.1brs1H,5.96brs1H,6.39 brd(6.5)1H,6.97s1H,7.33m5H, 7.38m10H. |
| 9 | " | " | " | —COCH₂S-Tet | 3420,1789,1726,1682, 1630,1601,1586. | 2.03s3H,2.26s3H,3.52s2H,3.93 s3H,4.17s2H,4.34s1H,4.65d(6) 1H,5.09s1H,6.40d(6)1H,7.00s1H 7.00-7.53m15H. |
| 10 | " | Ph | " | —CH=CH₂ | 3420,1770,1715,1670. | 2.07s3H,2.27s3H,4.10brd2H, 4.95q(6.1)1H,5.88d(1)1H,6.95 brd2H,5.85m1H,6.63d(6)1H,7.00 s1H,7.17-7.67m15H. |
| 11 | " | " | " | —C(=CHCOOCH₃)CH₂S-Tet | 3425,1777,1720,1665, 1604,1180. | 2.03s3H,2.22s3H,3.58s3H,3.82 s3H,4.21brs4H,4.82d(6.5)1H, 5.10s1H,5.83s1H,6.80s1H,7.00 -7.50m15H. |
| 12 | Ia | " | " | —CH=CH₂ | 3425,1775,1745,1665, 1600. | 1.83s3H,4.13brd2H,4.87d(6.0) 1H,5.05m2H,5.25s1H,5.83m1H, 6.00m1H,6.67brd1H,6.91s1H, 7.00-7.50m15H. |
| 13 | Ib | " | CH₂Ph | " | 1765,1720,1660. | 2.05s3H,2.28s3H,4.15brd(6.0) 2H,5.02d(8.0)1H,5.0-5.52m5H, 5.52-6.22m1H,7.2-7.9m11H. |
| 15 | Ia | CH₂OPh | C(CH₃)₃ | —C≡CH | 3410,3300,2110,1780, 1735,1690. | 1.55s9H,1.90s3H,2.45t(3)1H, 4.38d(3)2H,4.55s2H,4.71d0.5H, 4.83s1H,5.13s2H,5.41s1H, 7.60-6.75m6H. |

*mp. 112.5-114° C.

EXAMPLE 16

(A) Diphenylmethyl α-[4(R)-acetonyloxy-3(R)phenylacetamido-2-oxo-azetidin-1-yl]-α-isopropylideneacetate To a solution of diphenylmethyl α-[4(R)-propargyloxy-3(R)-phenylacetamido-2-oxo-azetidin-1-yl]-α-isopropylideneacetate (2.236 g; 4.28 mmole) in methanol (20 ml) is added water (2 ml). To this solution is added a saturated solution of mercuric sulfate in 10% sulfuric acid (0.8 ml), and the mixture is refluxed for 30 minutes. The reaction mixture is cooled, diluted with ethyl acetate, and washed with water. The ethyl acetate layer is dried over sodium sulfate, and concentrated under reduced pressure. Purification of the residue by chromatography over silica gel containing 10% water (100 g) using a mixture of benzene and ethyl acetate (2:1) as eluting solvent gives the product.

(B) Diphenylmethyl α-[4(R)-acetonyloxy-3(R)phenylacetamido-2-oxo-azetidin-1-yl]glyoxalate To a solution of diphenylmethyl α-[4(R)-acetonyloxy-3(R)-phenylacetamido-2-oxo-azetidin-1-yl]-α-isopropylideneacetate (2.342 g; 4.33 mmoles) in methylene chloride (40 ml) is introduced ozonized oxygen for 25 minutes at −78° C. Excess ozone is purged with nigrogen gas, and the mixture is mixed with dimethyl sulfide (3 ml), and stirred at −78° C. for 30 minutes, and at room temperature for 30 minutes. The reaction mixture is mixed with three drops of acetic acid, washed with water, dried over sodium sulfate, and evaporated under reduced pressure to give the product.

(C) Diphenylmethyl α-[4(R)-acetonyloxy-3(R)phenylacetamido-2-oxo-azetidin-1-yl]glycolate To a solution of diphenylmethyl α-[4(R)-acetonyloxy-3(R)-phenylacetamido-2-oxo-azetidin-1-yl]glyoxalate (2.312 g) in a mixture of methylene chloride (10 ml) and glacial acetic acid (10 ml) is added activated zinc powder (2.50 g) with stirring, and the mixture is stirred for 3 hours at room temperature. The reaction mixture is filtered through a layer of Celite which is washed with methylene chloride. The filtrate is washed with water, dried over sodium sulfate, and evaporated under reduced pressure to give the product as a mixture of epimers at position α.

(D) Diphenylmethyl α-[4(R)-acetonyloxy-3(R)phenylacetamido-2-oxo-azetidin-1-yl]-α-chloroacetate To a solution of diphenylmethyl α-[4(R)-acetonyloxy-3(R)-phenylacetamido-2-oxo-azetidin-1-yl]glycolate (2.136 g) in anhydrous methylene chloride (20 ml) are added thionyl chloride (0.90 ml) and pyridine (0.33 ml) with stirring at 0° C. After stirring for 1 hour at 0° C., the mixture is poured into ice water, and extracted with ethyl acetate. The organic layer is washed with water, dried over sodium sulfate, and evaporated under reduced pressure to give the crude product of a mixture of epimers at position α.

(E) Diphenylmethyl α-[4(R)-acetonyloxy-3(R)phenylacetamido-2-oxo-azetidin-1-yl]-α-triphenylphosphoranylideneacetate To a solution of crude diphenylmethyl α-[4(R)-acetonyloxy-3(R)-phenylacetamido-2-oxo-azetidin-1-yl]-α-chloroacetate (2.251 g) in anhydrous methylenechloride (20 ml) is added triphenylphosphine (1.50 g), and the mixture is refluxed for 4 hours under nitrogen atmosphere. The reaction mixture is poured into ice water, mixed with 5% aqueous solution of sodium hydrogen carbonate (20 ml), and extracted with methylene chloride. The organic layer is washed with water, dried over sodium sulfate, and evaporated under reduced pressure. Purification of the residue by chromatography over silica gel containing 10% water (100 g) using a mixture of benzene and ethyl acetate (1:2) as eluting solvent gives the product.

(F) Diphenylmethyl 1-oxadethia-3-methyl-7-phenylacetamido-3-cephem-4-carboxylate A solution of diphenylmethyl α-[4(R)-acetonyloxy-3(R)-phenylacetamido-2-oxazetidin-1-yl]-α-triphenylphosphoranylideneacetate (2.328 g) in anhydrous dioxane (30 ml) is refluxed for 64 hours under nitrogen atmosphere, and evaporated under reduced pressure to remove dioxane. The residue is purified by chromatography over silica gel containing 10% water (150 g) using a mixture of benzene and ethyl acetate (1:1) as developing solvent to give the product.

(G) Diphenylmethyl 1-oxadethia-3-methyl-7α-methoxy-7β-phenylacetamido-3-cephem-4-carboxylate To a solution of diphenylmethyl 1-oxadethia-3-methyl-7-phenylacetamido-3-cephem-4-carboxylate (371 mg) in methylene chloride (5 ml) cooled to −35°–40° C. are added a solution of lithium methoxide in methanol (0.5 ml, 2 mmole/1 ml) and then after 10 minutes acetic acid (0.2 ml). The mixture is then poured into water, and extracted with methylene chloride. The extract is washed with aqueous solutions of sodium hydrogen carbonate, sodium sulfate and sodium chloride, successively, dried over magnesium sulfate, and evaporated to dryness. The residue is chromatographed on 10% water-containing silica gel (20 g) to yield the product.

What we claim is:

1. A compound of the formula:

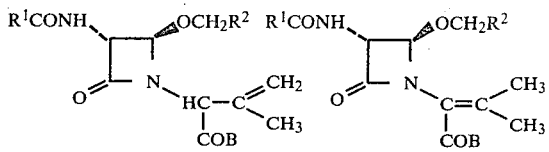

wherein
$R^1$ is $C_{1-5}$ alkyl, phenoxy-$C_{1-3}$ alkyl, phenyl-$C_{1-3}$- alkyl, phenyl, tolyl, methoxyphenyl, chlorophenyl, nitrophenyl, hydroxyphenyl, acetoxyphenyl, acetamidophenyl, thienyl or furyl;

$R^2$ is ethynyl, 2-bromoethynyl, acetoxyacetyl, (1-methyl-tetrazol-5-yl)thioacetyl, (2-methyl-1,3,4-thiadiazol-5-yl)thioacetyl, 1-methylene-2-acetoxyethyl, 1-methylene-2-(1-methyltetrazol-5-yl) thioethyl, 1-methylene-2-(2-methyl-1,3,4-thiadiazol-5-yl)-thioethyl or 1-methoxycarbonylmethylene-2-(1-methyl-tetrazol-5-yl) thioethyl;

and B is hydroxy, $C_{1-4}$ alkoxy, phenyl-$C_{1-3}$ alkoxy, diphenyl-$C_{1-3}$ alkoxy, phenoxy, indanyloxy, naphthoxy, tri-$C_{1-3}$ alkylsilyloxy, $C_{1-3}$ alkoxy di-$C_{1-3}$ alkylsilyloxy, tri-$C_{1-3}$ alkylstannyloxy, di-$C_{1-3}$ alkylhydrazino, alkali metal oxy, magnesium oxy, calcium oxy, aluminum oxy, tri-$C_{1-3}$ alkylammonium oxy or bicyclohexylammonium oxy.

2. A compound claimed in claim 1, wherein B is hydroxy, phenyl-$C_{1-3}$ alkoxy, diphenyl-$C_{1-3}$ alkoxy or $C_{1-4}$ alkoxy.

3. A compound claimed in claim 2, wherein $R^1$ is methyl, benzyl, phenoxymethyl or phenyl.

4. A compound claimed in claim 3, wherein $R^2$ is ethynyl, 2-bromoethynyl, (1-methyltetrazol-5-yl)thioacetyl, 1-methylene-2-acetoxyethyl or 1-methoxycarbonylmethylene-2-(1-methyltetrazol-5-yl)thioethyl.

5. A compound claimed in claim 3, wherein $R^2$ is acetoxyacetyl.

6. A compound claimed in claim 4, wherein B is hydroxy, diphenylmethoxy, benzyloxy or t-butoxy.

7. A compound claimed in claim 1, wherein $R^1$ is benzyl or phenyl; $R^2$ is ethynyl; and B is diphenylmethoxy.

8. A compound claimed in claim 1, wherein $R^1$ is benzyl, $R^2$ is ethynyl and B is diphenylmethoxy.

9. A compound claimed in claim 1, wherein $R^1$ is phenyl, $R^2$ is bromoethynyl and B is diphenylmethoxy.

10. A compound claimed in claim 1, wherein $R^1$ is benzyl, $R^2$ is acetoxyacetyl and B is diphenylmethoxy.

11. A compound claimed in claim 1, wherein $R^1$ is benzyl, $R^2$ is bromoethynyl and B is diphenylmethoxy.

12. A compound claimed in claim 1, wherein $R^1$ is phenyl, $R^2$ is acetoxyacetyl and B is diphenylmethoxy.

* * * * *